United States Patent
Demharter et al.

(10) Patent No.: US 9,151,810 B2
(45) Date of Patent: Oct. 6, 2015

(54) DEVICE AND METHOD FOR SYNCHRONIZING MAGNETIC RESONANCE UNIT WITH THE CARDIAC RHYTHM OF A PATIENT

(75) Inventors: Nikolaus Demharter, Dormitz (DE); Jürgen Rößler, Münnerstadt (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 1654 days.

(21) Appl. No.: 11/983,861

(22) Filed: Nov. 13, 2007

(65) Prior Publication Data

US 2008/0114237 A1    May 15, 2008

(30) Foreign Application Priority Data

Nov. 14, 2006    (DE) .................. 10 2006 053 613

(51) Int. Cl.
- *G01R 33/28* (2006.01)
- *A61B 5/00* (2006.01)
- *A61B 5/0456* (2006.01)
- *G01R 33/567* (2006.01)
- *A61B 5/055* (2006.01)

(52) U.S. Cl.
CPC .............. *G01R 33/28* (2013.01); *A61B 5/0456* (2013.01); *A61B 5/7285* (2013.01); *A61B 5/7292* (2013.01); *G01R 33/5673* (2013.01); *A61B 5/055* (2013.01)

(58) Field of Classification Search
CPC .... A61B 5/055; A61B 5/7285; A61B 5/0456; A61B 5/7292; G01R 33/28; G01R 33/5673
USPC ............... 600/407, 411, 413, 300; 382/128
See application file for complete search history.

(56) References Cited

U.S. PATENT DOCUMENTS

| | | | | | |
|---|---|---|---|---|---|
| 4,887,609 | A | * | 12/1989 | Cole, Jr. ................. | 600/509 |
| 4,991,587 | A | * | 2/1991 | Blakeley et al. .......... | 600/483 |
| 5,987,348 | A | * | 11/1999 | Fischer et al. ............ | 600/413 |
| 6,073,039 | A | * | 6/2000 | Berson ..................... | 600/372 |
| 2006/0122490 | A1 | * | 6/2006 | Sha et al. ................. | 600/413 |
| 2007/0092123 | A1 | * | 4/2007 | Popescu ................... | 382/128 |

FOREIGN PATENT DOCUMENTS

WO    9904688 A1    2/1999

OTHER PUBLICATIONS

Fisher et al., "Novel Real-Time R-Wave Detection Algorithm Based on the Vectorcardiogram for Accurate Gated Magnetic Resonance Acquisitions", Magnetic Resonance in Medicine, vol. 42, 1999, pp. 361-370.*

Deklerck et al.; "An ECG Trigger Module for the Acquisition of Cardiac MR Images"; Computers in Cardiology 1994 Bethesda, MD, USA, Sep. 25-28, 1994, pp. 533-536; Los Alamitos, CA, USA; IEEE Comput. Soc. US.

* cited by examiner

*Primary Examiner* — Katherine Fernandez

(57) ABSTRACT

The invention relates to a device for synchronizing a magnetic resonance unit with the cardiac rhythm of a patient, comprising a number of electrodes for leading off electrocardiogram signals from the body of the patient and an evaluation unit for determining a characteristic trigger time within a cardiac rhythm period of the patient from the electrocardiogram signals. In order to provide a device, which allows reliable determination of characteristic trigger times within the cardiac rhythm period of the patient even with elevated magnetic field strengths and which operates at least largely independently of external magnetic fields, it is proposed that the evaluation unit is designed to compare electrocardiogram signals obtained before and after the introduction of the patient into the magnetic resonance unit, in order to determine an enlargement of at least one characteristic of the electrocardiogram signals due to the magnetic field.

6 Claims, 2 Drawing Sheets

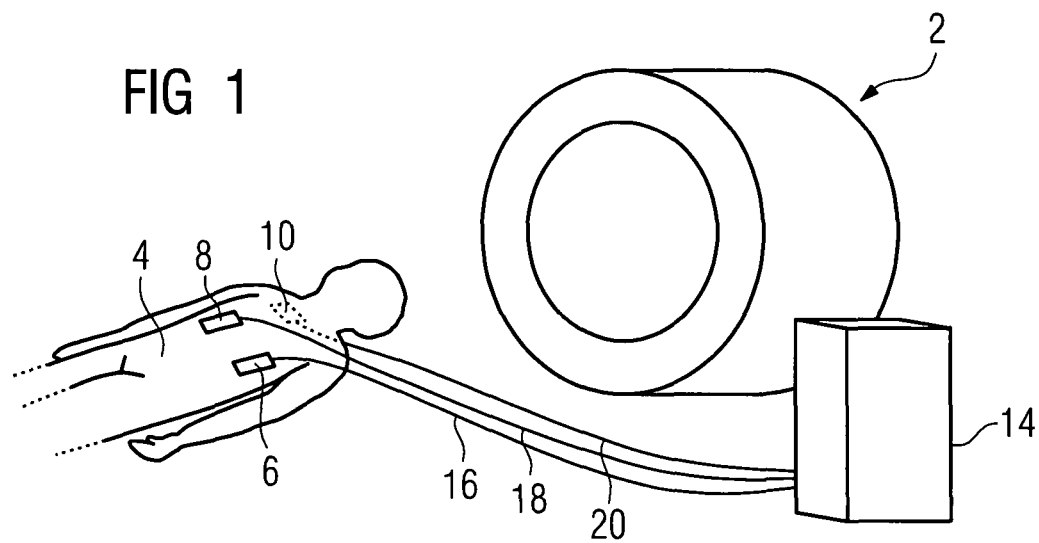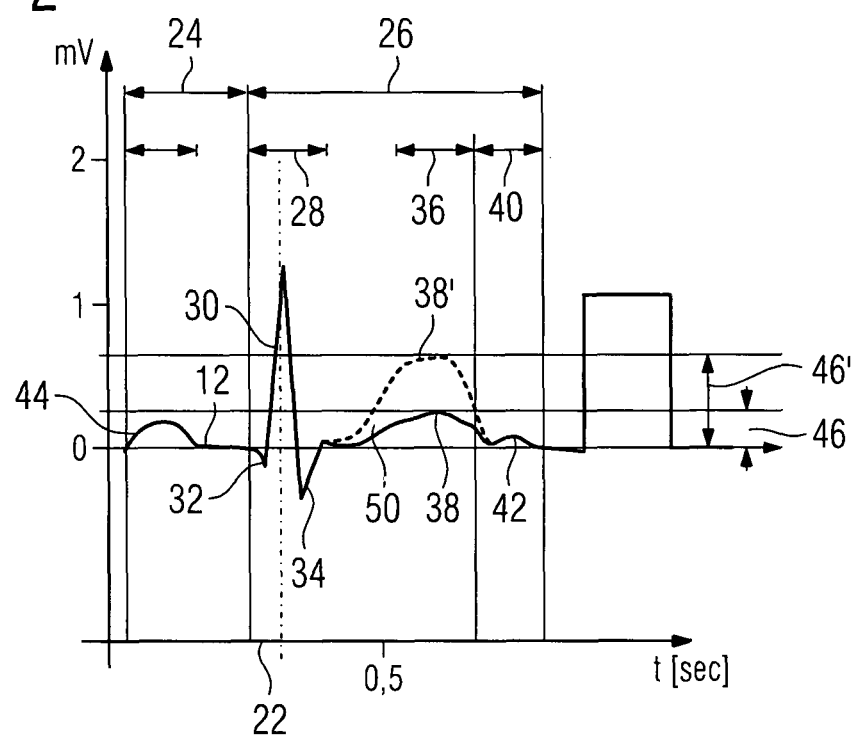

DEVICE AND METHOD FOR SYNCHRONIZING MAGNETIC RESONANCE UNIT WITH THE CARDIAC RHYTHM OF A PATIENT

CROSS REFERENCE TO RELATED APPLICATIONS

This application claims priority of German application No. 10 2006 053 613.4 filed Nov. 14, 2006, which is incorporated by reference herein in its entirety.

FIELD OF THE INVENTION

The invention relates to a device and a method for synchronizing a magnetic resonance unit with the cardiac rhythm of a patient by determining a characteristic trigger time within a cardiac rhythm period of the patient from the electrocardiogram signals of electrodes.

BACKGROUND OF THE INVENTION

Devices are known from the field, which serve to synchronize a magnetic resonance unit with the cardiac rhythm of a patient. In addition to the electrodes of an electrocardiogram device these have an evaluation unit for determining a characteristic trigger time within a cardiac rhythm period of the patient from the electrocardiogram signals of the electrodes. The characteristic trigger time is determined by a simple trigger threshold within the rising or falling edge of the R wave of the electrocardiogram signal. Synchronization serves to prevent motion artifacts, which can be produced, if the magnetic resonance recording takes place in different phases within the periodic motion of the heartbeat.

While the known methods and devices operate sufficiently reliably in the magnetic field-free space, in the magnetic resonance high field a significantly enlarged T wave can result in the ventricle part of the electrocardiogram signal compared with the field-free electrocardiogram due to the magnetohydrodynamic effect acting on the turbulences in the ventricle, so that the amplitude of the T wave can reach the trigger threshold. This significantly impedes automatic identification of the R wave.

SUMMARY OF THE INVENTION

The object of the invention is in particular to provide a device and method, which allow reliable determination of characteristic trigger times within the cardiac rhythm period of the patient even with elevated magnetic field strengths.

The object directed at the device is achieved by a device for synchronizing a magnetic resonance unit with the cardiac rhythm of a patient, comprising a number of electrodes for leading off electrocardiogram signals from the body of the patient and an evaluation unit for determining a characteristic trigger time within a cardiac rhythm period of the patient from the electrocardiogram signals, in which the evaluation unit is designed according to the invention to compare electrocardiogram signals obtained before and after the patient is introduced into the magnetic resonance unit, in order to determine an enlargement of at least one characteristic of the electrocardiogram signals due to the magnetic field. This allows the influence of the magnetic field of the magnetic resonance unit on the characteristics of the electrocardiogram signals to be determined and taken into account when synchronizing the magnetic resonance unit with the cardiac rhythm of a patient.

The enlargement can also be used as an additional criterion for differentiating different characteristics of the electrocardiogram (ECG), so that diagnosis errors can be avoided. The influence of the magnetic field can largely be eliminated, thereby allowing the device to be independent of external magnetic fields. This ultimately ensures reliable determination of characteristic trigger times within the cardiac rhythm period of the patient even with elevated magnetic field strengths and makes it possible to prevent the characteristics being confused.

Characteristics of the electrocardiogram signals in this context are all the characteristics of the time pattern of the electrocardiogram signals frequently used by those skilled in the art and able to be detected reliably by means of electronic data processing, in particular maxima, minima, gradients or waves. Specifically the characteristics considered are the P wave in the atrium part and the R wave and T wave in the ventricle part of the electrocardiogram signal. The electrode lead-offs can be bipolar or unipolar lead-offs. The inventive device can be deployed in conjunction with magnetic resonance and/or nuclear spin tomography. The evaluation unit can be an evaluation and trigger unit, which also carries out a triggering operation as well as evaluating a trigger time.

In an advantageous refinement of the invention the device comprises at least three electrodes for leading off electrocardiogram signals from the body of the patient. It is possible to obtain detailed information about cardiac activity and it is possible in particular to generate a three-dimensional vector cardiogram from the signals. The direction, in which the external magnetic field predominantly distorts the three-dimensional vector cardiogram, can be at least largely eliminated by means of a simple projection operation. The different possible views or projections of a three-dimensional vector cardiogram can provide information, which allows clear differentiation of the different characteristics. The selection of a view or projection, in which magnetohydrodynamic effects only have a minor influence, can easily be facilitated.

In a further refinement of the invention it is proposed that the evaluation unit is designed, to determine the characteristic trigger time as a function of the result of the comparison of the electrocardiogram signals before and after the introduction of the patient into the magnetic resonance unit, to select one characteristic of the electrocardiogram signal from a number of characteristics of the electrocardiogram signal. From the changes in the magnetic field-dependent characteristics it is possible to determine their type. In particular the T wave, whose amplitude increases significantly due to magnetohydrodynamic effects when a strong magnetic field is applied, can be differentiated from the R wave, which is largely independent of the magnetic field.

If the evaluation unit is designed to generate a number of vector cardiograms with a smaller dimension from a higher dimension vector cardiogram by means of projection operations, it is possible to reduce the influence of the magnetic field in a particularly simple manner, by selecting the projection direction so that it is as parallel as possible to the direction, in which the magnetic field predominantly acts on the three-dimensional vector cardiogram.

The influence of the magnetic field can hereby be kept small, if the evaluation unit is provided to select the vector cardiogram showing the smallest changes when the electrocardiogram signals before and after the introduction of the patient into the magnetic resonance unit are compared from the number of vector cardiograms with a smaller dimension for synchronizing the magnetic resonance unit with the cardiac rhythm of the patient.

The evaluation unit is advantageously designed to select one channel or group of channels of the electrocardiogram signals for determining the characteristic trigger time as a function of the result of the comparison of the electrocardiogram signals before and after the introduction of the patient into the magnetic resonance unit. It is then possible to reduce the influence of the magnetic field in a particularly simple manner. For example it is possible to select only that channel or those channels, which show the smallest changes when the electrocardiogram signals before and after the introduction of the patient into the magnetic resonance unit are compared.

In the specific instance where the influence of the magnetic resonance unit on all the channels of the electrocardiogram signals is approximately equal however all the channels for determining the characteristic trigger time can be selected.

The parameter used for the magnetic field-dependent changes can be the amplitude, the square of the difference between amplitude patterns before and after the introduction of the patient or another parameter that appears expedient to the person skilled in the art.

The evaluation unit is hereby particularly advantageously designed in such a manner that it selects the channel or group of channels for determining the characteristic of the electrocardiogram signals, whose enlargement due to the magnetic field, in particular in respect of the T wave, is the smallest.

It is also proposed that the evaluation unit should be designed, to determine an enlargement of the characteristic of the electrocardiogram signals configured as a T wave, to compare the height of the T wave of the electrocardiogram signals before and after the introduction of the patient into the magnetic resonance unit. The height of the maximum of the T wave is a parameter that is simple to capture, which is extremely dependent on the magnetic field due to the magnetohydrodynamic effects, and which is therefore particularly suitable as a parameter for identifying the T wave.

Alternatively or additionally the evaluation unit for determining an enlargement of the characteristic of the electrocardiogram signals configured as a T wave can compare a gradient of the T wave of the electrocardiogram signals before and after the introduction of the patient into the magnetic resonance unit. The gradient is similarly magnetic field-dependent and easy to detect and can be determined in the rising edge or the falling edge. In order to obtain a reliable and reproducible value, the gradient is particularly advantageously determined at the turning point of the respective edge.

Even though in principle the selection of the characteristic or the location of the R wave can also be effected on the basis of the time patterns of the electrode signals, this process can be significantly simplified, if the evaluation unit is designed to generate at least a two- or multi-dimensional vector cardiogram from the electrocardiogram signals. The two- or multi-dimensional vector cardiogram has the advantage of clarity.

If the evaluation unit is designed, to determine the characteristic trigger time within a cardiac rhythm period of the patient as a function of the comparison of the ECG signals, to select a characteristic of the electrocardiogram signals, which shows a smaller enlargement due to the magnetic field than at least one other characteristic, it is possible to achieve a device that is largely independent of the external magnetic field of the magnetic resonance unit.

The object directed at the method is achieved by a method for synchronizing a magnetic resonance unit with the cardiac rhythm of a patient by determining a characteristic trigger time within a cardiac rhythm period of the patient from the electrocardiogram signals of electrodes, in which according to the invention, to determine an enlargement of at least one characteristic of the electrocardiogram signals due to the magnetic field before and after the introduction of the patient into the magnetic resonance unit, electrocardiogram signals obtained are compared. It is possible to determine the influence of the magnetic field of the magnetic resonance unit on the characteristics of the electrocardiogram signals and take it into account when synchronizing the magnetic resonance unit with the cardiac rhythm of a patient.

BRIEF DESCRIPTION OF THE DRAWINGS

The invention is described in more detail with reference to exemplary embodiments shown in the drawings, in which:

FIG. 1 shows a schematic diagram of a magnetic resonance unit with a device for synchronizing the magnetic resonance unit with the cardiac rhythm of a patient, FIG. 2 shows an electrocardiogram signal with different characteristics.

DETAILED DESCRIPTION OF THE INVENTION

Figure 3:
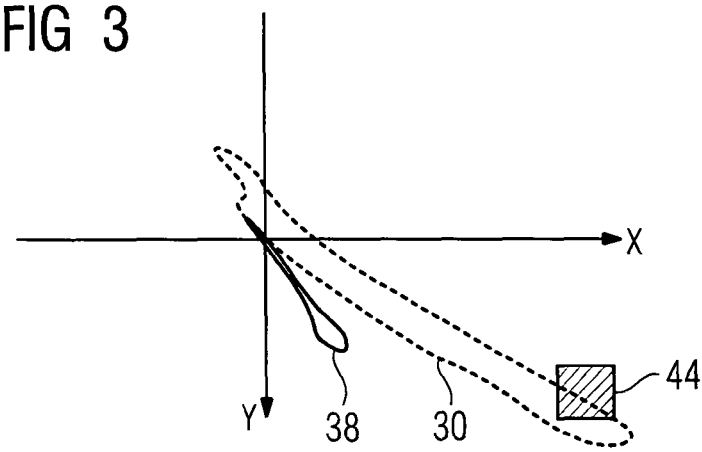
FIG. 3 shows a two-dimensional vector cardiogram with a T wave and an R wave.

FIG. 1 shows a schematic diagram of a device for synchronizing a magnetic resonance unit 2 with the cardiac rhythm of a patient 4. The device comprises a number of electrodes 6, 8, 10 for leading off electrocardiogram signals 12 (FIG. 2) from the body of the patient 4 and an evaluation unit 14 for determining a characteristic trigger time 22 (FIG. 2) within a cardiac rhythm period of the patient 4 from the electrocardiogram signals 12 of the electrodes 6, 8, 10. The evaluation unit 14 is configured as a single piece with the control unit of the magnetic resonance unit 2.

The control unit uses the trigger signals to synchronize the recording of magnetic resonance images by the magnetic resonance unit 2 with the cardiac rhythm of the patient 4, thus avoiding motion artifacts, by acquiring different recordings respectively in the same phase of the cardiac rhythm period.

The evaluation unit 14 is designed by a suitable program, whose function is described in more detail below, to determine an enlargement of at least one characteristic of the electrocardiogram signals 12 due to the magnetic field, to compare the electrocardiogram signals 12 before and after the introduction of the patient 4 into the magnetic resonance unit 2.

In the exemplary embodiment shown in FIG. 1 the device comprises three electrodes 6, 8, 10 for leading off electrocardiogram signals 12 from the body of the patient 4. The three electrodes 6, 8, 10 are attached in such a manner that the lead-offs are as perpendicular as possible to each other. The three electrodes 6, 8, 10 are used to pick off voltages, which are assigned respectively to a channel. The evaluation unit 14 picks off the voltages present at the electrodes 6, 8, 10 directly by way of cables 16, 18, 20 in each instance.

To determine the characteristic trigger time 22 (FIG. 2), the evaluation unit 14 selects one characteristic of the electrocardiogram signal 12 from a number of characteristics of the electrocardiogram signal 12 as a function of the result of the comparison of the electrocardiogram signals before and after the introduction of the patient 4 into the magnetic resonance unit 2.

FIG. 2 shows a typical electrocardiogram signal 12 of a patient 4 in the magnetic field-free space. The electrocardiogram is made up of an atrium part 24 and a ventricle part 26.

The atrium part 24 is assigned to the contraction of the atrium and has a P wave 44 as its characteristic. The ventricle part 26 starts with a so-called QRS phase 28, the primary characteristic of which is the central R wave 30, which is framed by a preceding Q wave 32 with reverse polarization and a subsequent S wave 34 with reverse polarization. The ventricle part 26 also comprises a T phase 36 with a T wave 38 and a U phase 40 with a U wave 42. Without any magnetic field the amplitude of the T wave 38 is around ⅙ to ⅔ of the amplitude of the R wave 30 and the amplitude of the Q wave 32 is less than ¼ of the amplitude of the R wave 30. The magnitude of the amplitude of the R wave 30 is around 1 mV. In comparison the amplitude of the P wave 44 is below 0.25 mV.

In FIG. 2 an enlarged T wave 38', as shown after the introduction of the patient into the magnetic resonance unit 2, is marked with a broken line. On the right next to the actual electrocardiogram signal 12 is a calibration wave with a height of 1 mV.

The evaluation unit 14 uses the detected electrocardiogram signals 12 to calculate a three-dimensional vector cardiogram, with the signal of each channel or each of the three electrodes 6, 8, 10 forming a component of a three-dimensional vector. In the three-dimensional vector cardiogram every characteristic of the electrocardiogram signal 12 has a correspondence in a loop in the resulting curve, which the point in the cardiac rhythm of the patient 4 defined by the three-dimensional vector periodically passes through.

In a further refinement of the invention the evaluation unit 14 carries out projection operations to generate a number of vector cardiograms with a smaller dimension from one higher dimension vector cardiogram. By way of example FIG. 3 shows a two-dimensional vector cardiogram, generated by means of a projection operation onto the X-Y plane from the three-dimensional vector cardiogram. In FIG. 3 the larger loop, which appears dotted due to the high speed of motion of the point, represents the R wave 30, while the smaller, narrow loop represents the T wave 38.

In the three-dimensional vector cardiogram the differences between the R wave 30 and the T wave 38 are clearly identifiable, also because the T wave 38 increases significantly on application of the high field of the magnetic resonance unit 2. To determine the characteristic trigger time 22 within a cardiac rhythm period of the patient 4, the evaluation unit 14 selects one characteristic of the electrocardiogram signals 12, the R wave 30, which shows a smaller enlargement due to the magnetic field than the T wave 38. This selection is made by selecting a specific loop in the three-dimensional vector cardiogram. Since the T loop responds in a more sensitive manner to the magnetic field than the R wave 30, the characteristic thus selected corresponds reliably to the R wave 30.

To determine the characteristic trigger time 22, the evaluation unit 14 specifies a point or region 44 defined by angle and distance from source or by three coordinate values on the loop corresponding to the R wave 30. If the vector moving on the loop reaches this region 44, the trigger is activated. Activation of the trigger determines the characteristic trigger time 22.

The evaluation unit 14 selects from the three two-dimensional vector cardiograms (FIG. 3, 4a, 4b) for synchronizing the magnetic resonance unit 2 with the cardiac rhythm of the patient 4 obtained by the projections onto the coordinate planes the vector cardiogram which shows the smallest changes when the electrocardiogram signals 12 before and after the introduction of the patient 4 into the magnetic resonance unit 2 are compared. The selected two-dimensional vector cardiogram (FIG. 3) is assigned to the projection plane, which is at the largest angle to the longitudinal axis of the loop of the three-dimensional vector cardiogram, which maps the T wave 38.

Figure 4A:
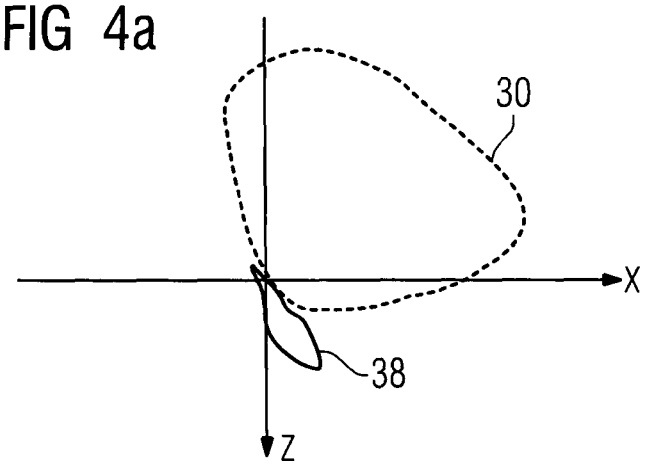
FIG. 4a shows a first two-dimensional projection of a three-dimensional vector cardiogram and FIG. 4b shows a second two-dimensional projection of a three-dimensional vector cardiogram.
Figure 4B:
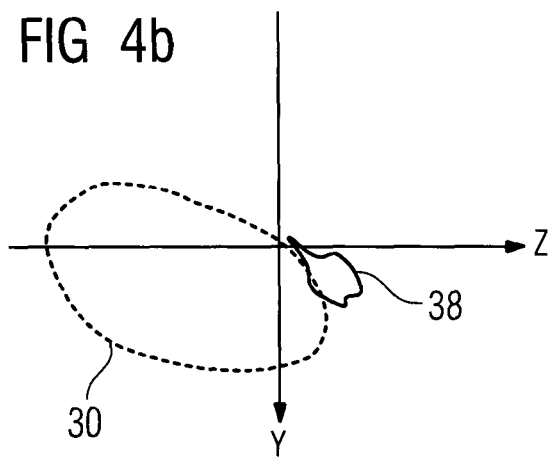

FIGS. 4a and 4b show the two further two-dimensional vector cardiograms, obtained in addition to the selected vector cardiogram shown in FIG. 3 by projection onto the coordinate planes from the three-dimensional vector cardiogram. FIG. 4a here shows the projection onto the sagittal plane or the X-Z plane and FIG. 4a shows the projection onto the cranial plane or the Y-Z plane. Once the suitable projection has been selected, the actual trigger process takes place by evaluating the movement of the vector determined by the electrode signals in the two-dimensional diagram. The region 44 or point defining the trigger threshold is projected onto the two-dimensional plane with the path curve.

In alternative refinements of the invention it is possible to obtain two-dimensional vector cardiograms by projections onto further projection planes that are different from the coordinate planes. The projection plane can be selected by forming the minimum of the suitably selected parameter for changes in the electrocardiogram signals 12.

In a further alternative refinement of the invention the evaluation unit 14 is designed to select one channel or a group of channels of the electrocardiogram signals 12 for determining the characteristic trigger time 22 as a function of the result of the comparison of the electrocardiogram signals 12 before and after the introduction of the patient 4 into the magnetic resonance unit 2. Selection of the channel replaces selection of the projection plane, with selection of a projection plane from the three coordinate planes naturally corresponding to a selection of a pair of channels.

If the device comprises more than 3 electrodes 6, 8, 10, such that a higher dimension vector cardiogram is generated in a higher dimension vector space, projection onto a corresponding hyperplane or lower space can be achieved by channel selection. For example it is possible to obtain four three-dimensional vector cardiograms and/or six two-dimensional vector cardiograms by means of projections from one four-dimensional vector cardiogram, etc.

The evaluation unit 14 is hereby programmed in such a manner that it selects the channel or group of channels for determining the characteristic of the electrocardiogram signals 12, whose enlargement due to the magnetic field is smallest. The maximum difference between or the mean, optionally squared difference between the signals before and after the introduction of the patient 4 into the magnetic resonance unit 2 can for example be selected as the parameter for the enlargement due to the magnetic field.

Since the T wave 38 responds in a particularly sensitive manner to the external magnetic field, when the channel or group of channels is being selected, the data processing algorithm of the evaluation unit 14 concentrates in particular on the response of the T wave 38. This is achieved in that the evaluation unit 14 for determining an enlargement of the T wave 38 compares the height 46 of the same in the electrocardiogram signals 12 before the introduction of the patient 4 and the height 46' after the introduction of the patient 4 into the magnetic resonance unit 2 or forms the difference between the two determined heights 46, 46'.

Alternatively or additionally in a development of the invention to determine an enlargement of the T wave 38 an increase in the T wave 38 of the electrocardiogram signals 12 before and after the introduction of the patient 4 into the magnetic resonance unit 2 is compared or the difference between the two determined increases is formed. To this end the evaluation unit 14 first determines the turning point 50 of the rising edge 48 of the T wave 38 and then determines the rise in the turning point 50.

Ultimately the device described above implements a method for synchronizing a magnetic resonance unit 2 with the cardiac rhythm of a patient 4 by determining a characteristic trigger time 22 within a cardiac rhythm period of the patient 4 from the electrocardiogram signals 12 of electrodes 6, 8, 10.

In the inventive method, to determine an enlargement of at least one characteristic of the electrocardiogram signals 12, the electrocardiogram signals 12 before and after the introduction of the patient 4 into the magnetic resonance unit 2 are compared.

The invention claimed is:

1. A method for synchronizing a magnetic resonance unit with a cardiac rhythm of a patient, comprising:
    obtaining electrocardiogram signals of the patient by at least three electrodes respectively, wherein the at least three electrodes are arranged so that the electrocardiogram signals are perpendicular to each other;
    calculating a three-dimensional vector cardiogram from the electrocardiogram signals, wherein characteristics of the electrocardiogram signals comprise correspondences in loops in the three-dimensional vector cardiogram,
    generating three two-dimensional vector cardiograms by projecting the three-dimensional vector cardiogram onto three two-dimensional planes;
    selecting a characteristic of the electrocardiogram signals by selecting a specific loop in the three-dimensional vector cardiogram that is less sensitive to a magnetic field of the magnetic resonance unit than other loops;
    comparing the electrocardiogram signals obtained before introducing the patient into the magnetic resonance unit and after introducing the patient into the magnetic resonance unit in the three two-dimensional vector cardiograms;
    selecting a two-dimensional vector cardiogram from the three two-dimensional vector cardiograms having a smallest change based on the comparison,
    defining a region on the specific loop corresponding to the selected characteristic in the selected two-dimensional vector cardiogram;
    activating a trigger if a vector moving on the specific loop reaches the region in the selected two-dimensional vector cardiogram;
    determining a characteristic trigger time within the cardiac rhythm of the patient based on the activation of the trigger; and
    triggering the magnetic resonance unit based on the characteristic trigger time for synchronizing the magnetic resonance unit with the cardiac rhythm of the patient for a magnetic resonance recording to prevent motion artifacts in different phases within a period motion of heartbeat of the patient.

2. The method as claimed in claim 1, wherein the characteristic of the electrocardiogram signals is selected from a plurality of characteristics of the electrocardiogram signals.

3. The method as claimed in claim 1, wherein a channel or a group of channels of the electrocardiogram signals is selected for determining a characteristic of the electrocardiogram signals having a smallest change.

4. The method as claimed in claim 1, wherein selecting the characteristic comprises determining enlargement of the characteristic of the electrocardiogram signals by comparing a height of characteristics of the electrocardiogram signals before and after the introduction of the patient into the magnetic resonance unit.

5. The method as claimed in claim 1, wherein selecting the characteristic comprises determining an enlargement of the characteristic of the electrocardiogram signals by comparing a gradient of characteristics of the electrocardiogram signals before and after the introduction of the patient into the magnetic resonance unit.

6. The method as claimed in claim 1, wherein at least one two-dimensional vector cardiogram is generated from the electrocardiogram signals.

* * * * *